US007604812B2

(12) United States Patent
Franke

(10) Patent No.: US 7,604,812 B2

(45) Date of Patent: Oct. 20, 2009

(54) HYPOALLERGENIC AND NON-IRRITANT SKIN CARE FORMULATIONS

(75) Inventor: Patrick Franke, McNair-Promenade 124, Berlin (DE) 14167

(73) Assignee: Patrick Franke, Berlin (DE)

( * ) Notice: Subject to any disclaimer, the term of this patent is extended or adjusted under 35 U.S.C. 154(b) by 774 days.

(21) Appl. No.: 10/450,666

(22) PCT Filed: Dec. 14, 2001

(86) PCT No.: PCT/EP01/14825

§ 371 (c)(1),
(2), (4) Date: Nov. 28, 2003

(87) PCT Pub. No.: WO02/47642

PCT Pub. Date: Jun. 20, 2002

(65) Prior Publication Data

US 2004/0081674 A1 Apr. 29, 2004

Related U.S. Application Data

(60) Provisional application No. 60/255,379, filed on Dec. 15, 2000.

(30) Foreign Application Priority Data

Dec. 15, 2000 (EP) .................................. 00127555

(51) Int. Cl.
*A61K 8/02* (2006.01)
*A61K 8/18* (2006.01)

(52) U.S. Cl. ........................................ 424/401; 424/59

(58) Field of Classification Search .................. 424/401
See application file for complete search history.

(56) References Cited

U.S. PATENT DOCUMENTS

| | | | | |
|---|---|---|---|---|
| 4,832,858 | A * | 5/1989 | Vishnupad et al. | 508/110 |
| 5,017,605 | A * | 5/1991 | Stindl | 514/529 |
| 5,552,147 | A | 9/1996 | Znaiden | |
| 5,561,166 | A | 10/1996 | Sattler | |
| 5,599,533 | A * | 2/1997 | Stepniewski et al. | 424/78.02 |
| 5,688,831 | A * | 11/1997 | El-Nokaly et al. | 424/401 |
| 5,783,176 | A | 7/1998 | Meiring et al. | |
| 5,863,546 | A * | 1/1999 | Swinehart | 424/401 |
| 5,919,398 | A * | 7/1999 | Nakamura et al. | 516/104 |
| 6,235,271 | B1 * | 5/2001 | Luther et al. | 424/59 |
| 6,248,354 | B1 * | 6/2001 | Firestone et al. | 424/451 |
| 6,328,984 | B1 | 12/2001 | Katsuyama | |
| 6,419,938 | B1 * | 7/2002 | Riedel et al. | 424/401 |
| 2002/0077372 | A1 * | 6/2002 | Gers-Barlag et al. | 516/98 |
| 2003/0072723 | A1 * | 4/2003 | Gers-Barlag et al. | 424/59 |

FOREIGN PATENT DOCUMENTS

| | | |
|---|---|---|
| DE | 19810011 * | 9/1999 |
| DE | 19843876 A | 4/2000 |
| EP | 0847750 A | 6/1998 |
| EP | 1115365 A1 | 9/1999 |
| JP | 5-001298 | 1/1993 |
| JP | 6500079 | 1/1994 |
| JP | 812519 | 1/1996 |
| JP | 9132511 | 5/1997 |
| JP | 09-176006 | 7/1997 |
| JP | 10-045561 | 2/1998 |
| JP | 10175839 | 6/1998 |
| JP | 10-218724 | 8/1998 |
| JP | 10-298092 | 11/1998 |
| JP | 11-193207 | 7/1999 |
| JP | 11-302152 | 11/1999 |
| JP | 2000-016937 | 1/2000 |
| JP | 2000109421 | 4/2000 |
| JP | 2000264829 | 9/2000 |
| JP | 2000302673 | 10/2000 |
| WO | WO 9300085 | 1/1993 |
| WO | WO 9817246 | 4/1998 |
| WO | WO 0018357 | 4/2000 |

OTHER PUBLICATIONS

Kanehara Yoshihide, "Moisture-keeping protective agent for skin," Patent Abstracts of Japan, Apr. 18, 2000, Publication No. 2000-109421.

Kurimura Hajime et al., "Emulsion Composition," Patent Abstracts of Japan, Sep. 26, 2000, Publication No. 2000-264829.

Ichii Yuji et al., "Skin External Preparation Composition," Patent Abstracts of Japan, Jan. 16, 1996, Publication No. 08-012519.

Patent Abstracts of Japan, "Skin lotion originated from cow's milk and its production," Nov. 2, 1999, JP11-302152.

Patent Abstracts of Japan, "Preparation for external use only," Jul. 21, 1999, JP 11-193207.

Patent Abstracts of Japan, "Anti-itchy lotion," Apr. 3, 1997, JP10-298092.

Patent Abstracts of Japan, "Water for cosmetic," Feb. 7, 1997, JP 10-218724.

Patent Abstracts of Japan, "Soap," Jan. 8, 1993, JP 05-001298.

Examintation Report, Japanese patent office.

Patent Abstracts of Japan, "Parasiticide for Hatchery Fish," Jan. 18, 2000, JP2000-016937.

(Continued)

*Primary Examiner*—Sreeni Padmanabhan
*Assistant Examiner*—Umamaheswari Ramachandran
(74) *Attorney, Agent, or Firm*—Millen, White, Zelano, Branigan, P.C.

(57) ABSTRACT

The invention provides novel hypoallergenic and non-irritant medical skin care formulations being water-in-oil emulsions. The formulations are free from ingredients with a known allergenic potential, such as fragrances, preservatives, colorings, plant extracts, PEGs, cetylstearyl alcohol, lanolin alcohol, lower alcohols and proteins, thus being particularly suitable for patients with sensitive dry skin. The skin care formulations of the invention are useful in the prophylaxis and treatment of dry, sensitive skin or in the therapy or therapy support of eczematous or psoriatic skin and exhibit favorable sensorial properties. The invention furthermore provides a method of manufacturing the novel hypoallergenic and non-irritant skin care formulations.

15 Claims, No Drawings

OTHER PUBLICATIONS

Patent Abstracts of Japan, "Humectant Composition," Feb. 17, 1998, JP10-045561.

Patent Abstracts of Japan, "Base for Skin Preparation for External Use and Skin Preparation for External Use Containing the Base," Aug. 7, 1997, JP09-176006.

ABIN.: "Final Report on the safety assessment of Cetearyl Octanoate" J. American College of Toxicology, vol. 1, No. 4, 1982, pp. 81-90, XP000982324.

Kaidbey K. Photomaximization test for identifying photoallergic contact sensitizers, *Contact Dermatitis* 1980:6:161-169.

Watsky et al, 1992, Cutis 50, 383-386.

"Dry Skin and Moisturizers:Chemistry and Function" p. 403 Eds. Loden and Maibach, 2000.

:"Unwanted effects of cosmetics and drugs in dermatology" pp. 6-10. Eds. DeGroot, Weyland and Nater, 1994.

* cited by examiner

HYPOALLERGENIC AND NON-IRRITANT SKIN CARE FORMULATIONS

This application is a National Stage entry of PCT/EP01/14825 filed on 14 Dec. 2001, and claims priority to U.S. Provisional Application Ser. No. 60/255,379, filed 15 Dec. 2000.

FIELD OF THE INVENTION

This invention relates to hypoallergenic and non-irritant skin care formulations. The formulations of the invention are particularly suitable for medical applications such as for treating dry, sensitive skin and for therapy of skin conditions such as eczema and psoriasis. The formulations of the invention are compliance-friendly and superior to previously known formulations claiming to be hypoallergenic and non-irritant.

BACKGROUND OF THE INVENTION

Human skin acts as a barrier and protective layer against chemical, physical and mechanical insults. The primary function of the skin's outer layer—the horny layer—is to prevent loss of water and vital substances into the environment while keeping noxious exogenous materials from penetrating to living tissue. The person skilled in the art refers to the outer horny layer as the stratum corneum (SC). Other functions of the SC include regulation of homeostatic mechanisms to assure steady-state conditions in the face of a changing environment, mechanisms of repair after disruption of the barrier by disease or exogenous insults and the presence of antibacterial substances to protect against infection. In order to fulfill these functions, the SC needs to be hydrated and flexible.

Complicated mechanisms in the skin maintain the essential hydration state of the SC. However, many factors work to compromise the SC barrier and increase the rate of water loss. Exposure to harsh conditions, including cold, dry winter weather, frequent washing with soap and hot water, exposure to surfactants or irritating chemicals or solvents may cause skin dryness. Apart from external factors provoking dry skin conditions, several diseases are known that are characterized by an abnormal condition or behavior of the SC. Examples of these diseases are atopic dermatitis, psoriasis and ichthyosis.

The SC sheds clusters of cells known as corneocytes from the surface of the skin while continuously replenishing them from underlying layers. This process is usually imperceptible due to the small size of the clusters, but in dry skin, the larger aggregates of these cells are shed as scales or flakes. Dry skin is characterized by a rough, dry feeling and flaky appearance. It may itch and become red and irritated, and persons suffering from very dry skin (xerosis) may scratch affected areas repeatedly. If such conditions are untreated, severely dry skin may crack and bleed. Accumulation of thick brittle scales may occur such as in psoriasis and various forms of ichthyosis.

Skin moisturizers are used to help prevent skin from becoming dry or to return dry skin to its normal condition. Several compounds are known to act as skin moisturizers or humectants. Among these are glycerol (glycerin), urea, petrolatum (petroleum jelly), polyethylene glycols (PEGs), lanolins (wool wax), lactic acid (lactate), and ceramides. In skin care products, these ingredients are formulated together with a large variety of other ingredients used for maximizing efficacy, stability and shelf life. For skin care products, the subjective impressions of the user are particularly important.

Thus, ingredients for improving subjective properties such as stickiness/greasiness, distribution/spreading, absorption, odor, or color are also added. Typically, skin care products are comprised of about 20-50 different ingredients, since it is the experience of the personal skilled in the art that favorable results may not be achieved by formulations with fewer ingredients.

The ingredients of skin care formulations are generally combined to form an emulsion, since they consist of hydrophobic and hydrophilic ingredients. In principle, two basic types of emulsions are possible. In an oil-in-water (O/W) emulsion, the oil phase forms the discontinuous phase, whereas in a water-in-oil (W/O) emulsion, the water phase represents the discontinuous phase.

Most skin care products are formulated as O/W emulsions. O/W emulsions are usually preferred for cosmetics, due to their favorable cosmetic properties that are pleasing for consumers. An O/W emulsion however represents a trade off in favor of such user-pleasing properties, since O/W-emulsions are generally less effective than W/O emulsions in treating or ameliorating dry skin conditions.

It has been suggested that W/O emulsions are suitable as an adjunctive therapy in the treatment of psoriasis, thus providing a steroid-sparing effect (Watsky et al., 1992, *Cutis* 50, 1992). In U.S. Pat. No. 5,561,166, Sattler et al., a W/O composition containing urea and salts of lactic acid for the treatment of dry skin was disclosed. Additionally, U.S. Pat. No. 5,552,147 discloses cosmetic compositions containing alpha hydroxy carboxylic acids dispersed in petroleum jelly with the aid of a phosphatide.

A common problem associated with skin care products is that they cause adverse effects in consumers or patients. Such unwanted effects include irritation (subjective and objective), allergic contact dermatitis, photocontact dermatitis, and immediate contact reactions ("*Dry Skin and Moisturizers: Chemistry & Function*", p. 403, Eds. Loden & Maibach, 2000). In this context, it should be understood that irritant reactions are distinct to allergenic reactions due to their different characteristics and/or mode of action. Established techniques such as patch testing are known to those skilled in the art and can be used to differentiate between the two types of reaction (see e.g., "*Unwanted effects of cosmetics and drugs used in dermatology*", pp. 6-10, Eds. de Groot, Weyland and Nater, Elsevier 1994).

The most frequently observed side effect is allergic contact dermatitis. This reaction is usually caused by fragrances and preservatives present in these products. Another origin of allergic reactions are moisturizers such as lanolin and its derivatives, emulsifiers such as cocamidopropyl betaine, and emollients.

Although many of the ingredients typically used in skin care formulations have a known irritation or allergenic sensitization potential and the rate of allergenic reactions in consumers or patients has increased dramatically over the last few years, these ingredients are still used in the majority of products in the skin care market of today. Several skin care formulations claim to be low in certain allergens and/or irritants. U.S. Pat. No. 5,863,546 discloses cosmetic compositions, which differ significantly from the skin formulations of the invention, that exclude certain allergens and irritants.

The prior art has failed to provide a skin care formulation that avoids irritant and allergenic ingredients but retains favorable properties, in particular in the field of medical skin care. This may be attributed to the fact that strictly avoiding such ingredients undermines other desired properties such as effective moisturizing of dry skin, stability of the formulation and favorable sensory attributes from the point of the view of the patient/consumer.

Accordingly, there is a need for a hypoallergenic and non-irritant skin care formulation that effectively moisturizes dry, sensitive skin while at the same time exhibiting physical/microbiological stability and meeting the subjective aesthetic expectations of the patient/consumer.

OBJECT AND SUMMARY OF THE INVENTION

It is an object of the present invention to solve the problems associated with available and known skin care formulations by providing a hypoallergenic and non-irritant skin care formulation. Aside from being hypoallergenic and non-irritant, the formulations of the invention effectively moisturize dry, sensitive skin and are stable and pleasing to the patient/consumer. The formulations of the invention are suitable for medical skin care, such as for the therapy or therapy support of psoriasis and eczema.

The formulations of the invention are free from ingredients such as perfumes or perfume substitutes (fragrances), preservatives, colorings, plant extracts, polyethylene glycols (PEGs), cetylstearyl alcohol, lanolin alcohols, lower alcohols, proteins and other substances with known allergenic potential, thus being particularly suitable for patients with sensitive skin. However, it is noted that the term "free from ingredients with known allergic potential" is intended to mean that such substances are not purposefully included in the formulations, although they might be present in very limited amounts, e.g. as a contaminant of other ingredients. Since the allergenic and/or irritant potential of the ingredients is generally known to be dependent on their concentration, it should be understood that the presence of very limited amounts of such ingredients is still meant to be within the scope of the present invention.

The formulations of the invention comprise a water phase dispersed in an oil phase. In this embodiment, the oil phase may comprise cetearyl octanoate, dicaprylyl ether, caprylic/capric triglyceride, polyglyceryl-3-diisostearate and polyglyceryl-2-dipolyhydroxystearate.

In one aspect of the invention, the formulations have relatively few ingredients, preferably less than 15, most preferably 12 or 13 ingredients.

In another aspect of the invention, the water phase of the formulations comprises the ingredients purified water, magnesium sulfate, lactic acid and sodium lactate. Additionally, the water phase may further comprise glycerin.

In one embodiment, the oil phase of the formulation may further comprise petrolatum and cera alba. Additionally, the oil phase may comprise ethylhexylglycerin or, alternatively, the water phase may further comprise propylene glycol.

In a second embodiment, the oil phase may further comprise ethylhexylglycerin. In this second embodiment, the water phase may further comprise urea.

The invention furthermore provides a method of manufacturing the hypoallergenic and non-irritant skin care formulations of the invention. It also provides formulations further comprising one or more pharmaceutically active compounds, vitamins or vitamin analogs, and/or a sunscreen, as well as formulations for use in the prophylaxis and treatment of dry, sensitive skin or in the therapy of eczematous or psoriatic skin.

It is another object of the invention to provide a method for the prophylaxis and treatment of dry, sensitive skin or for therapy support of eczematous skin and psoriatic skin by topically administering a therapeutically effective amount of the dermatological skin care formulations of the present invention.

DETAILED DESCRIPTION OF THE INVENTION

The invention provides hypoallergenic and non-irritant skin care formulations having superior properties. The formulations of the invention, exemplary embodiments of which are described in more detail below, are particularly suitable for medical skin care and for the treatment of dry, sensitive skin. Despite being free from such ingredients as perfumes or perfume substitutes, preservatives, colorings, plant extracts, PEGs, cetylstearyl alcohol, lanolin alcohol, lower alcohols and proteins, the formulations of the invention unexpectedly retain many desirable properties.

Although many of the ingredients commonly used in skin care formulations are not present, the skin care formulations of the invention are highly effective with maximal skin tolerance. For the formulations, the inventor chose raw materials with a proven skin tolerance and a high physicochemical and microbiological stability. Focusing on the properties of the individual ingredients, the inventor selected a mixture of skin lipids on the basis of sensorial properties, tactility and polarity. Furthermore, in order to overcome the problems of the prior art, substances with known allergenic or irritant potential were eliminated and only selected ingredients, preferably possessing multifunctional properties, and modern types of biodegradable emulsifiers are employed. These formulations exhibit a high degree of dispersity and are suitable for application in climate zone IV.

Though suitable for medical use, the skin care formulations of the invention have favorable cosmetic properties, such as excellent absorption, lack of stickiness, scent, and oily shine. This is evidenced by the results of sensory assessment studies performed with several embodiments of the invention (see Table 3).

The formulations of the invention furthermore exhibit excellent physical/microbiological stability (see Example 4) and fulfill the requirements of the cosmetic directives of the European Union and the United States. The formulations are physicochemically stable and meet the United States Pharmacopeia (USP) requirements in terms of microbiological stability. Although free of any preservatives, a shelf life of at least 2 years can be expected for the formulations of the invention.

In a preferred embodiment of the present invention, the skin care formulation is in the form of a semi-solid formulation (cream), which is particularly suitable for topical application to the face. Such a formulation is preferably a W/O emulsion.

The following table lists the ingredients of such a preferred formulation of the invention wherein each ingredient may be present in an amount independently of the amount of the other according to the ranges given in the table below and expressed as percent by weight (% w/w).

| | | preferred | More preferred | most preferred |
|---|---|---|---|---|
| (A) oil phase | | | | |
| petrolatum | 1-6% | 2-5% | 2.5-4% | 2.75-3.5% |
| cetearyl octanoate | 1-6% | 2-5% | 2.5-4% | 2.75-3.5% |
| dicaprylyl ether | 1-5% | 1-3% | 2-3% | 2.5-3% |
| caprylic/capric | 4-12% | 5-10% | 7-9% | 7.5-8.5% |

-continued

| | | preferred | More preferred | most preferred |
|---|---|---|---|---|
| triglyceride | | | | |
| cera alba | 0.5-4% | 1.0-2.5% | 1.5-2.5% | 1.75-2.25% |
| polyglyceryl-3-diisostearate | 3-6% | 4-5% | 4.25-4.75% | 4.4-4.6% |
| polyglyceryl-2-di-polyhydroxy-stearate | 0.5-3% | 1-2% | 1.25-1.75% | 1.4-1.6% |
| ethylhexyl-glycerin | 0-1% | 0-0.8% | 0.2-0.6% | 0.25-0.5% |
| (B) water phase | | | | |
| glycerin | 0-7% | 0-5% | 2-4% | 2.5-3.5% |
| magnesium sulfate | 0.2-2% | 0.5-1.5% | 0.8-1.2% | 0.9-1.1% |
| lactic acid | 0-2% | 0.05-1.5% | 0.05-0.5% | 0.05-0.25% |
| sodium lactate | 0.5-6% | 1-5% | 1.5-2.5% | 1.6-2.0% |
| purified water | add to 100% | add to 100% | add to 100% | add to 100% |

In a second preferred embodiment, the semi-solid (cream) formulation comprises the following ingredients, wherein each ingredient may be present in an amount independently of the amount of the other according to the ranges given in the table below and expressed as percent by weight (% w/w).

| | | preferred | More preferred | most preferred |
|---|---|---|---|---|
| (A) oil phase | | | | |
| petrolatum | 1-6% | 2-5% | 2.5-4% | 2.75-3.5% |
| cetearyl octanoate | 1-6% | 2-5% | 2.5-4% | 2.75-3.5% |
| dicaprylyl ether | 1-5% | 1-3% | 2-3% | 2.5-3% |
| caprylic/capric triglyceride | 4-12% | 5-10% | 7-9% | 7.5-8.5% |
| cera alba | 0.5-4% | 1.0-2.5% | 1.5-2.5% | 1.75-2.25% |
| polyglyceryl-3-diisostearate | 3-6% | 4-5% | 4.25-4.75% | 4.4-4.6% |
| polyglyceryl-2-di polyhydroxy-stearate | 0.5-3% | 1-2% | 1.25-1.75% | 1.4-1.6% |
| (B) water phase | | | | |
| glycerin | 0-7% | 0-5% | 2-4% | 2.5-3.5% |
| magnesium sulfate | 0.2-2% | 0.5-1.5% | 0.8-1.2% | 0.9-1.1% |
| lactic acid | 0-2% | 0.05-1.5% | 0.05-0.5% | 0.05-0.25% |
| sodium lactate | 0.5-6% | 1-5% | 1-3% | 1-2.5% |
| propylene glycol | 4-12% | 5-10% | 7-9% | 7.5-8.5% |
| purified water | add to 100% | add to 100% | add to 100% | add to 100% |

Preferably, the above formulation is a W/O emulsion. It is also particularly suitable for application to the face.

In a third preferred embodiment of the invention, the skin care formulation is in the form of a semi-liquid (lotion) formulation (preferably W/O) which is suitable for topical application to the whole body. Each ingredient may be present in an amount independently of the amount of the other according to the ranges given in the table below and expressed as percent by weight (% w/w).

| | | preferred | More preferred | most preferred |
|---|---|---|---|---|
| (A) oil phase | | | | |
| cetearyl octanoate | 1-8% | 2-5% | 3.5-5% | 4.5-5% |
| dicaprylyl ether | 1-5% | 1-3% | 2-3% | 2.5-3% |
| caprylic/capric triglyceride | 6-20% | 8-15% | 12-15% | 14-15% |
| polyglyceryl-3-diisostearate | 1-4% | 1.5-3% | 1.75-2.25% | 1.9-2.1% |
| polyglyceryl-2-di polyhydroxy-stearate | 2-6% | 3-5% | 3.5-4.5% | 3.75-4.25% |
| ethylhexyl-glycerin | 0-1% | 0-0.8% | 0.2-0.6% | 0.25-0.5% |
| (B) water phase | | | | |
| glycerin | 0-6% | 0-5% | 2-4% | 2.5-3.5% |
| magnesium sulfate | 0.25-2% | 0.5-1.5% | 0.8-1.2% | 0.9-1.1% |
| lactic acid | 0-2% | 0.05-1.5% | 1-1.4% | 1.2-1.3% |
| sodium lactate | 0.5-7% | 1-5% | 3-4.5% | 3.25-4.25% |
| urea | 0.5-12% | 0.5-10% | 3-7% | 4-6% |
| purified water | add to 100% | add to 100% | add to 100% | add to 100% |

It should be understood that the above-mentioned percentages or percentage ranges given for the ingredients of the formulations according to the invention may be subject to small variations (e.g., due to varying degrees of purity of the ingredients) without departing from the spirit of the invention.

However, the ingredients used for the dermatologic formulations of the invention should be of high quality and purity.

The hypoallergenic and non-irritant skin care formulations of the invention are suitable as emollients, for therapy or therapy support of eczematous and psoriatric skin, as well as for therapeutic daily skin care treatment of dry, sensitive skin.

Furthermore, the formulations of the invention may further comprise one or more of the ingredients selected from a sunscreen, a vitamin or vitamin analog, such as Vitamin E, Vitamin K, Calcipotriol, Tacalcitol, or a pharmaceutically active compound, such as corticoids, antimycotics, immunosuppressants, salicylic acid, alpha- or beta-hydroxy acids, or linolenic acid.

The group of corticoids may include but is not limited to hydrocortisone and derivatives thereof, such as methylprednisolone aceponate, diflucortolone valerate, fluocortolone pivalate/hexanoate/monohydrate, fluocortinbutyl, betamethasone and derivatives thereof, clobetasole, triamcinolone acetonide, dexamethasone, prednisolone, and clocortolone pivalate. The group of antimycotics may include but is not limited to ketoconazole, isoconazole, miconazole, and clotrimazole; and the group of immunosuppressants may include but is not limited to ascomycin and derivatives thereof, cyclosporine A, azathioprine, methotrexate, cyclophosphamide, and the like.

The invention furthermore provides a robust and easily applicable method of manufacturing the skin care formulations of the invention. Manufacturing of the skin care formulations is achieved by preparing the oil phase by melting the ingredients of the oil phase such as cetearyl octanoate, dicaprylyl ether, caprylic/capric triglyceride, polyglyceryl-3-diisostearate, polyglyceryl-2-dipolyhydroxystearate, petrolatum, cera alba, and ethylhexylglycerin, with stirring until all ingredients are completely melted. The ingredients chosen for the oil phase will depend on the oil phase that is desired, as described above.

For the water (aqueous) phase, purified water is heated in a separate vessel and the ingredients of the water phase such as magnesium sulfate, sodium lactate, lactic acid, and optionally glycerin, urea, and propylene glycol, are added depending upon the desired composition of the water phase (see above, for example). Such ingredients are dissolved with stirring and subsequently, the pH value of the resulting solution is adjusted with lactic acid to about 4.4-4.8. Both the oil and water phase are preferably heated to about 75-85° C. during melting and dissolution, respectively.

Prior to the combination of the oil and the water phase, the oil phase is filtered through filter cartridges with 0.1 mm filter units for particulate filtration. Subsequently, the emulsion is prepared by transferring the melted oil phase as prepared above to the heated water phase and, while stirring and homogenizing, cooling the emulsion down under vacuum conditions, preferably about −0.6 to −0.9 bar, to room temperature.

Preferably, the oil phase is transferred into the water phase while stirring at about 40 $min^{-1}$ at 75-85° C., cooled down to about 58-62° C. while stirring and homogenizing at 3000 $min^{-1}$, further cooled to about 38-42° C. while stirring and homogenizing at 4000 $min^{-1}$, and finally cooled down to about 23-27° C. while stirring. After the cooling process, the prepared semi-solid or semi-liquid W/O emulsions of the present invention can be discharged into appropriate containers.

The invention is further illustrated in the Examples. The Examples are not intended to limit the scope of the invention.

EXAMPLE 1

Preparation of Semi-Solid Formulation A

A semi-solid formulation according to the invention (designated Formulation A herein below) was prepared in a batch size of 50 kg using an ointment mixer and homogenizer (available under the trade name Becomix® RW 60 from Berents, Germany), equipped with a 60 L stainless steel pan, an infinitely variable anchor-type stirrer, homogenizer and process control system, a pH-meter, a stainless steel melting pan equipped with an infinitely variable stirrer, stainless steel ointment storage containers, and stainless steel sintered filter cartridges, 0.1 mm for particulate filtration.

For the preparation of the water phase, the ointment mixer/homogenizer was charged with 33.7 kg of purified water, 1.5 kg glycerin, 0.5 kg magnesium sulfate, and 0.992 kg sodium lactate and stirred (40 $min^{-1}$) at 80±2° C. until all components were completely dissolved. Subsequently, the pH value was checked and adjusted with 0.058 kg lactic acid to a pH of about 4.6.

The oil phase was prepared by charging the melting vessel with 1.5 kg petrolatum, 1.5 kg cetearyl octanoate, 1.5 kg dicaprylyl ether, 4.0 kg caprylic/capric triglyceride, 1.0 kg cera alba, 2.25 kg polyglyceryl-3-diisostearate, 0.75 kg polyglyceryl-2-dipolyhydroxystearate, and 0.15 kg ethylhexylglycerin and melted completely at 80±2° C. while stirring until no unmelted material remained visible. Finally, the oil phase was filtered through stainless steel filter cartridges with 0.1 mm filter units for particulate filtration prior to the addition to the water phase.

The emulsion was subsequently prepared by transferring the oil phase to the water phase in the ointment mixer/homogenizer with stirring (40 $min^{-1}$) at 80±2° C. The resultant mixture was then cooled to 60±2° C. while it was stirred and homogenized (3000 $min^{-1}$, cycle). The resulting emulsion was then further stirred and homogenized (4000 $min^{-1}$, cycle) during cooling to 40±2° C. Finally, stirring of the emulsion was continued until the emulsion had a temperature of 25±2° C. During the complete cool down process a vacuum of between −0.6 and 0.9 bar was applied.

The resulting cream was checked for homogeneity by microscopy for uniform appearance. After passing the homogeneity test, the product was discharged into bulk containers.

EXAMPLE 2

Preparation of Semi-solid Formulation B

Formulation B was prepared as formulation A, with the exception that 4 kg of propylene glycol was added to the water phase and no ethylhexylglycerin was added to the oil phase.

EXAMPLE 3

Preparation of Semi-liquid Formulation C

The semi-liquid formulation C was essentially prepared as formulations A and B in Examples 1 and 2. The differences in the manufacturing process are described below.

For the production of formulation C in a batch size of 50 kg, the ointment mixer/homogenizer was charged with 28.35 kg of purified water, 1.5 kg glycerin, 0.5 kg magnesium sulfate, 1.867 kg sodium lactate, and 2.5 kg urea and stirred (40 $min^{-1}$) at 80±2° C. until all components were completely dissolved. Subsequently, the pH value was checked and adjusted with 0.633 kg lactic acid to a pH of about 4.2.

The oil phase was prepared by charging the melting vessel with 2.5 kg cetearyl octanoate, 1.5 kg dicaprylyl ether, 7.5 kg caprylic/capric triglyceride, 1.0 kg polyglyceryl-3-diisostearate, 2.25 kg polyglyceryl-2-dipolyhydroxystearate, and 0.15 kg ethylhexyl-glycerin and melted completely at 80±2° C. while stirring until no unmelted material remained visible.

After particulate filtration, both phases were combined to form an emulsion as described in Example 1. After passing the homogeneity test, the resulting lotion was discharged into bulk containers.

EXAMPLE 4

Microbiological/physicochemical Stability

The formulations A, B, and C as prepared in Examples 1 to 3 were subjected to the following stability tests:

a) Storage at 4° C., 25° C., 30° C., 40° C., 50° C. at ambient humidity over 5 months
b) −4° C./50° C. cycle test over 2 weeks
c) Microbiological challenge test according to USP (United States Pharmacopeia) requirements The formulations were packaged in PE containers (HDPE/LDPE) in batch sizes of 2-25 kg and tested for parameters such as pH-value, viscosity (abs.), microscopic and macroscopic picture, content of urea (formulation C), and compatibility with the container material.

The test results showed that formulations A-C of Examples 1-3 are physicochemically stable under all tested conditions and meet the microbiological stability requirements of the USP.

EXAMPLE 5

Sensitization and Irritation Risk (HRIPT-Test)

A human repeated insult patch test (HRIPT) was carried out as a 40-days randomized, controlled, double-blind study to assess the sensitizing and irritating potential of the dermatological skin care formulations of the invention. The study was started with 58 healthy volunteers of either sex between 18 and 65 (ITT-cases: n=58), however, 3 volunteers dropped out and 55 volunteers completed the study (VC-cases: n=55).

In the induction phase (day 1-20), the volunteers were subjected to nine occlusive treatments for 24 hours with 75 μl of the test formulations as prepared in Examples 1-3 applied to their backs on days 1, 3, 5, 8, 10, 12, 15, 17, 19. Untreated test fields without application of a test formulation were used as a concurrent control. Skin reactions were evaluated 24 hours (½ hour after removal of test chambers; on days 2, 4, 6, 9, 11, 13, 16, 18, 20; nine readings) and 48 hours after the application of occlusive treatments on the backs of the volunteers (½ hour after removal of test chambers on days 3, 5, 10, 12, 17, 19; six readings) by a visual 6-point-score.

| Visual 6-point-score | |
|---|---|
| 0 | Negative/no reaction |
| 0.5 | Equivocal erythema |
| 1 | Erythema |
| 2 | Erythema and induration (edema) |
| 3 | Erythema, induration (edema) and vesicles |
| 4 | Erythema, induration (edema) and bullae and/or spreading |

The mean cumulative irritation index (M.C.I.I.) was calculated for the 24 hours readings (M.C.I.I./24 h.) and for the 48 hours readings (M.C.I.I./48 h.).

After the treatment-free interval (15 days; days 21-35; no treatment), an occlusive challenge application of the test formulations on yet untreated test sites on the backs of the volunteers was done for 24 hours. The test formulations were evaluated 24 h, 48 h, 72 h and 96 h after the application by the same visual 6-point score (challenge phase; 5 days, days 36-40).

Results:

Sensitization: No case of sensitization occurred in both ITT- and VC-population.

Irritation: No significant irritation potential in comparison to the empty untreated test field could be observed in both ITT- and VC-population.

Furthermore, no adverse events or serious adverse event related to the test formulations was observed during the course of the study.

EXAMPLE 6

Irritation Potential

The primary objective of this study was to evaluate the cutaneous tolerability of the skin care formulations of the invention over a 4-weeks period when used in the intended way (application twice daily to face or body, respectively) in the intended patient/consumer group having dry and sensitive skin. The secondary objectives of this study were to evaluate the irritation potential of the test formulations A and B when used around the eyes, to evaluate the hydrating effect of all test formulations as measured by corneometry, to evaluate the volunteer's general cosmetic acceptance of all test formulations, and finally to evaluate the cosmetic acceptance of the test formulations A and B as make-up foundations.

The study was designed as a single center, randomized study; double-blinded with interindividual comparison of treatments between the test formulations A, B, and comparative commercially available products for facial application and between test formulation C and comparative commercially available products for body application, and was performed for 28 consecutive days.

Healthy volunteers of either sex between 18 and 65 years old meeting specific inclusion/exclusion criteria with dry skin proven by low corneometer values (≦70) were chosen for this study. In addition, 50% of the volunteers were healthy individuals with atopic diathesis according to the atopy score of Diepgen without history for atopic dermatitis. The other 50% of the volunteers were without atopic diathesis. All volunteers in all treatment groups treated face and body twice daily at home over 28 consecutive days with the respective test formulations.

For the measurement of the hydrating effects of the test formulations for facial application, corneometry of both cheek bones was performed on days 1 and 29. For the test formulation for body application, corneometry of both anterior lower legs was performed on screen and on days 1 and 29.

A clinical assessment was performed at screen and on days 1, 8, 15 and 29 using a visual 5-point score (no/doubtful/slight/moderate/severe signs of irritation, erythema and/or scaling). Out of the results of the visual 5-point score an irritation product profile was created with four irritation groups being the primary variable of this study. Subjective symptoms were asked on days 8, 15 and 29 using a 5-point score for subjective evaluation (no/doubtful/slight/moderate/severe sensation of stinging/burning/pruritus with specification in case of any positive answer). Additionally, an ophthalmological examination investigating fore- and background of the eyes as well as the conjunctival mucosa and subjective ophthalmological symptoms using a 5-point score for subjective ophthalmological symptoms took place on days 1 and 29.

Additionally, a questionnaire concerning the sensorial profile and overall cosmetic acceptance (parameters: distribution/spreading, absorption, feeling on the skin, stickiness, greasiness, oily shine, odor, and color; evaluation on a 5-point scale) was filled in by the volunteers on day 29.

Results:

Table 1 summarizes the hydration effect as measured by corneometry of three embodiments of the invention (formulations A, B and C) in comparison to a reference product.

TABLE 1

Measurement of Hydration Effect by Corneometry

| Hydration effect (Corneometry) | Hydration improvement on Day 29 (in %) subgroup I (atopic subjects) | Hydration improvement on Day 29 (in %) subgroup II (non-atopic subjects) | Hydration improvement on Day 29 (in %) subgroup I + II |
|---|---|---|---|
| Formulation A (cream) | 43.1 | 21.0 | 32.1 |
| Formulation B (cream) | 31.2 | 39.1 | 35.1 |
| Formulation C (milk) | 38.6 | 45.7 | 42.2 |
| Reference product§ | 37.1 | 22.2 | 29.7 |

measured by corneometry of both cheek bones (Formulations A and B) and both anterior lower legs (Formulation C), respectively.

§commercially available W/O emulsion

In sum, application of the test formulations A, B and C for 28 days resulted in a significant hydration improvement between 32% and 42%, averaged over both subgroups (atopic and non-atopic subjects).

The results of the cutaneous tolerability study of formulations A, B, and C are summarized in Table 2. Tables 2(a) and (b) show the results of the dermatological and opthalmological investigations, respectively.

TABLE 2 (a)

Dermatological Investigation:

| Dermatological Investigation (ITT) | Face Formulations Formulation A | Face Formulations Formulation B | Body Formulation Formulation C |
|---|---|---|---|
| (1) Irritation profile: objective signs | 1/20 patients: moderate irritation and stop of treatment on day 14 | 1/20 patients: slight irritation; reduction of treatment dose | — |
| (2) Partial or transient stop of treatment related or possibly related to test formulation | | | — |
| Objective signs of irritation: (1) + (2) | 5% | 5% | — |
| (3) Irritation profile, subjective symptoms | 1/20 patients: slight pruritus | 2/20 patients: slight stinging 1/20 patients: slight pruritus | 2/19 patients: slight stinging |
| Subjective signs of irritation: (3) moderate or severe reactions | — | — | — |
| Mean Sum of irritation score | 0.10 ± 0.10 | 0.10 ± 0.10 | 0.00 ± 0.00 |
| Conclusion | Very good irritation profile | Excellent irritation profile | Excellent irritation profile |

TABLE 2 (b)

Ophthalmological Investigation

| Ophthalmological Investigation | Face Formulations Formulation A | Face Formulations Formulation B | Body Formulation Formulation C |
|---|---|---|---|
| Ophthalmologic objective symptoms | 1/20 patients: moderate conjunctival allergy left eye and mild conjunctival allergy right eye* | — | body formulation not tested around the eyes |
| Ophthalmologic subjective symptoms | 1/20 patients: moderate subjective symptoms* | 1/20 patients: slight itching tearing of left eye* | |
| Application interrupted or stopped due to ophthalmological symptoms | — | — | |
| Conclusion | Excellent tolerability of formulations when applied around the eyes | | |

*Subsequent studies demonstrated that the above symptoms were not caused by Formulations A and B.

As evident from the tabulated results, all tested dermatologic formulations of the invention exhibited a very good or even excellent irritation profile.

Additionally, the results of the questionnaire concerning the cosmetic acceptance of formulations A, B, and C are depicted in Tables 3(a)-(i). The following parameters were tested: overall cosmetic quality (Table 3(a)); distribution/spreading (Table 3(b)); absorption (Table 3(c)); feeling on the skin (Table 3(d)); stickiness (Table 3(e)); greasiness (Table 3(f)); oily shine (Table 3(g)); odor (Table 3(h)); color (Table 3(i)).

Table 3: Results of Sensory Assessment Tests

All values are given in % of volunteers.

TABLE 3 (a)

Overall opinion of the cosmetic qualities of formulations A-C

| Overall opinion | excellent | very good | good | acceptable | bad | no comment |
|---|---|---|---|---|---|---|
| Formulation A (cream) | 16 | 42 | 32 | 5 | 5 | 0 |
| Formulation B (cream) | 15 | 10 | 45 | 5 | 10 | 15 |
| Formulation C (lotion) | 26 | 16 | 37 | 5 | 11 | 5 |

TABLE 3 (b)

Distribution/Spreading

| Distribution/Spreading | very easy | easy | moderately easy | difficult | very difficult |
|---|---|---|---|---|---|
| Formulation A (cream) | 16 | 26 | 26 | 5 | 26 |
| Formulation B (cream) | 30 | 0 | 30 | 20 | 20 |
| Formulation C (lotion) | 11 | 5 | 16 | 11 | 58 |

TABLE 3 (c)

Absorption

| Absorption | very quick | quick | quite quick | slowly | very slowly | no comment |
|---|---|---|---|---|---|---|
| Formulation A (cream) | 26 | 11 | 26 | 11 | 26 | 0 |
| Formulation B (cream) | 30 | 15 | 10 | 15 | 25 | 5 |
| Formulation C (lotion) | 21 | 0 | 11 | 21 | 47 | 0 |

TABLE 3 (d)

Feeling on the skin

| Feeling on the skin | too light | light | just right | heavy | too heavy |
|---|---|---|---|---|---|
| Formulation A (cream) | 11 | 5 | 26 | 21 | 37 |
| Formulation B (cream) | 10 | 5 | 30 | 25 | 30 |
| Formulation C (lotion) | 5 | 5 | 11 | 21 | 58 |

TABLE 3 (e)

Stickiness

| Stickiness | not at all sticky | very few sticky | somewhat sticky | quite sticky | sticky |
|---|---|---|---|---|---|
| Formulation A (cream) | 26 | 5 | 37 | 11 | 21 |
| Formulation B (cream) | 15 | 10 | 45 | 15 | 15 |
| Formulation C (lotion) | 0 | 0 | 26 | 32 | 42 |

TABLE 3 (f)

| Greasiness | not at all greasy | very few greasy | somewhat greasy | quite greasy | greasy |
|---|---|---|---|---|---|
| | Greasiness | | | | |
| Formulation A (cream) | 11 | 5 | 32 | 42 | 11 |
| Formulation B (cream) | 15 | 0 | 20 | 55 | 10 |
| Formulation C (lotion) | 5 | 5 | 26 | 63 | 0 |

TABLE 3 (g)

| Oily shine | leaves no oily shine | leaves a very light oily shine | leaves a light oily shine | leaves an oily shine | leaves a very oily shine | No comment |
|---|---|---|---|---|---|---|
| | Oily shine | | | | | |
| Formulation A (cream) | 21 | 5 | 21 | 37 | 16 | |
| Formulation B (cream) | 15 | 0 | 25 | 20 | 40 | |
| Formulation C (lotion) | 16 | 0 | 11 | 37 | 32 | 5 |

TABLE 3 (h)

| Odor | no | yes, very light | yes, light | yes, moderate | yes, strong | yes, very strong |
|---|---|---|---|---|---|---|
| | Odor | | | | | |
| Formulation A (cream) | 53 | 16 | 21 | 0 | 5 | 5 |
| Formulation B (cream) | 40 | 35 | 15 | 5 | 5 | 0 |
| Formulation C (lotion) | 58 | 21 | 16 | 5 | 0 | 0 |

TABLE 3 (i)

| Color | very pleasant | pleasant | unpleasant | I don't care | no comment |
|---|---|---|---|---|---|
| | Color | | | | |
| Formulation A (cream) | 16 | 53 | 16 | 16 | 0 |
| Formulation B (cream) | 20 | 45 | 15 | 20 | 0 |
| Formulation C (lotion) | 16 | 53 | 26 | 5 | 0 |

EXAMPLE 7

Phototoxicity

In order to assess the phototoxic potential of the dermatologic skin care formulations of the invention, the semi-solid formulations of examples 1 and 2 were tested in a phototoxicity study running for 5 consecutive days. The study was designed as a single center, randomized, double-blind study with intraindividual comparison of treatments and interindividual comparison of treatments for the test formulations A and B. 12 healthy volunteers of either sex between 18 and 50 years old meeting specific inclusion/exclusion criteria were enrolled in the study. 50 μl of each test formulation was applied under occlusive conditions in duplicate on subject's back on days 1 for 24 hours. One duplicate test field without application of a formulations (empty test chamber with/without UV-radiation) was used as a control.

On day 1 and 2, the minimal erythema dose (MED) was assessed by irradiation of six small test fields with UVA/B on the upper back of the volunteer. The test chambers with the test formulations in duplicate were applied on day 1 to the designated test fields on both sides of the mid back of the volunteers. On day 2, the test chambers were removed after 24 hours and the test fields (20 J/cm$^2$ UVA+0.75×MED UVA+UVB) were irradiated on the left side of the mid back. The skin reactions were evaluated after one hour (day 2), after 24 hours (day 3), after 48 hours (day 4) and after 72 hours (day 5) using a 5-point visual score:

| Visual 5-point score | |
|---|---|
| 0 | No erythema |
| 0.5 | Equivocal erythema (barely perceptible erythema with no clearly defined border) |
| 1 | Mild but definite erythema with clearly defined border (MED) |
| 2 | Moderate, clearly defined erythema |
| 3 | Severe erythema, with or without infiltration |
| 4 | Severe erythema with vesicles or bullous reaction |

The number of volunteers who experienced a phototoxic reaction during the study determined the phototoxic potential of the test formulations.

Results: No case of phototoxicity could be observed with the dermatologic formulations A and B during the study in the test population.

EXAMPLE 8

Photo-Sensitization Risk

The primary objective of this study was to evaluate the photosensitizing potential of the dermatologic formulations of the invention in a population of n=25 healthy volunteers of either sex between 18 and 65 years with Fitzpatrick's skin type I, II, or III meeting specific inclusion/exclusion criteria using the modified method of Kaidbey & Kligman (Kaidbey & Kligman, 1980, *Contact Dermatitis* 6, 161-169). The secondary objective of this study was to evaluate the sensitization potential of the formulations.

The study was designed as a single center, randomized, double-blind study with intraindividual comparison of treatments and interindividual comparison of treatments for the test formulations including formulations A and B (cream) and was performed for 6 consecutive weeks. As a control, untreated test fields without application of test formulations were included into the study.

During the induction phase one series of test plasters with all test formulations and one empty field was fixed on the left sides of the backs. During the challenge phase two series of test plasters were fixed on each side of the back. Only the right side of the back was irradiated. Allocation of test formulations to test fields was identical for each volunteer during induction and challenge phase. For each application, 50 μl of the test formulation was applied under occlusive conditions on volunteers' backs on days 1, 4, 8, 11, 15, 18, and 36.

The MED of each subject was determined by irradiating increasing doses of UVA/UVB/with a solar simulator on previously selected sites of the volunteers back. Scoring was performed 24 hours after the irradiation. The MED is the smallest dose (mJ/$cm^2$) needed to induce a visible, clearly delineated erythema.

In the induction phase (20 days; day 1-20), six occlusive applications of one series of test formulations were done for 24 hours on the left side of the backs of volunteers on days 1, 4, 8, 11, 15, 18. After 24 h, the occlusive treatments were removed and all test fields were consecutively exposed to 3×MED UVA/UVB with a solar simulator on days 2, 5, 9, 12, 16, and 19. The results were evaluated 24 h after the irradiation by a 6-point visual score.

In the challenge phase (5 days; day 36-40) after the treatment-free interval (15 days; day 21-35), occlusive application of two series of test formulations on yet untreated sites on both sides of the backs of the volunteers were performed for 24 hours (challenge application). Consecutively, the test fields were exposed on the right side of the backs to 10 J/$cm^2$ UVA plus 0.75×MED (UVA/UVB) (challenge irradiation on day 37). The results were evaluated one hour after the challenge irradiation and additionally 24 h, 48 h and 72 h after challenge irradiation by a 6-point visual score.

The following 6-point visual score was used during induction and challenge phase:

| Visual 6-point-score | |
|---|---|
| 0 | No erythema |
| 0.5 | Equivocal erythema |
| 1 | Definite erythema with clearly defined border (MED) |
| 2 | Erythema with infiltration/papules |
| 3 | Erythema with vesicles or bullous reaction |
| 4 | Erythema with eroded bullous reaction and/or raised spreading reaction beyond the borders of the patch site |

Results: No case of photosensitization could be observed under the above-described conditions for the dermatological formulations A and B of Example 1 and 2 (facial formulations) in any of the volunteers.

The invention claimed is:

1. A hypoallergenic and non-irritant skin care formulation, wherein the formulation:

a) is free from fragrances, preservatives, colorings, plant extracts, PEGs, cetylstearyl alcohol, lanolin alcohol, lower alcohols and proteins; and b) comprises a water phase dispersed in an oil phase, wherein the oil phase comprises:
1-8 wt % cetearyl octanoate,
1-5 wt % dicaprylyl ether,
6-20 wt % caprylic/capric triglyceride,
1-4 wt % polyglyceryl-3-diisostearate and
2-6 wt % polyglyceryl-2-dipolyhydroxystearate,
wherein the water phase comprises:
purified water,
0.2-2 wt % magnesium sulfate,
0-2 wt % lactic acid and
0.5-7 wt % sodium lactate.

2. The skin care formulation according claim 1, wherein the water phase further comprises glycerin.

3. The skin care formulation according claim 1, wherein the oil phase further comprises ethylhexylglycerin.

4. The skin care formulation according claim 1, wherein the oil phase of the formulation further comprises petrolatum and cera alba.

5. The skin care formulation according to claim 4, wherein the oil phase further comprises ethylhexylglycerin.

6. The skin care formulation according to claim 4, wherein the water phase further comprises propylene glycol.

7. The skin care formulation according claim 1, wherein the water phase further comprises urea.

8. A semi-solid skin care formulation comprising the following ingredients expressed as a percent by weight (% w/w) range:

| | |
|---|---|
| (1) oil phase: | |
| a) petrolatum: | 2-5% |
| b) cetearyl octanoate: | 2-5% |
| c) dicaprylyl ether: | 1-3% |
| d) caprylic/capric triglyceride: | 5-10% |
| e) cera alba: | 1.0-2.5% |
| f) polyglyceryl-3-diisostearate: | 4-5% |
| g) polyglyceryl-2-dipolyhydroxystearate: | 1-2% |
| h) ethylhexylglycerin: | 0-0.8% |
| (2) water phase: | |
| a) glycerin: | 0-5% |
| b) magnesium sulfate: | 0.5-1.5% |
| c) lactic acid: | 0.05-1.5% |
| d) sodium lactate: | 1-5% |
| e) purified water: | add to 100%. |

9. A semi-solid skin care formulation, wherein the formulation comprises the following ingredients expressed as a percent by weight (% w/w) range:

| | |
|---|---|
| (1) oil phase: | |
| a) petrolatum: | 2-5% |
| b) cetearyl octanoate: | 2-5% |
| c) dicaprylyl ether: | 1-3% |
| d) caprylic/capric triglyceride: | 5-10% |
| e) cera alba: | 1.0-2.5% |
| f) polyglyceryl-3-diisostearate: | 4-5% |
| g) polyglyceryl-2-dipolyhydroxystearate: | 1-2% |
| (2) water phase: | |
| a) glycerin: | 0-5% |
| b) magnesium sulfate: | 0.5-1.5% |
| c) lactic acid: | 0.05-1.5% |
| d) sodium lactate: | 1-5% |
| e) propylene glycol: | 5-10% |
| f) purified water: | add to 100%. |

10. A semi-liquid skin care formulation comprising the following ingredients expressed as a percent by weight (% w/w) range:

| | |
|---|---|
| (1) oil phase: | |
| a) cetearyl octanoate: | 2-5% |
| b) dicaprylyl ether: | 1-3% |
| c) caprylic/capric triglyceride: | 8-15% |
| d) polyglyceryl-3-diisostearate: | 1.5-3% |
| e) polyglyceryl-2-dipolyhydroxystearate: | 3-5% |
| f) ethylhexylglycerin: | 0-0.8% |
| (2) water phase: | |
| a) glycerin: | 0-5% |
| b) magnesium sulfate: | 0.5-1.5% |
| c) lactic acid: | 0.05-1.5% |
| d) sodium lactate: | 1-5% |
| e) urea: | 0.5-10% |
| f) purified water: | add to 100%. |

11. The skin care formulation according claim 1, wherein the formulation further comprises one or more pharmaceutically active compounds, vitamins or vitamin analogs, and/or sunscreens.

12. The skin care formulation according to claim 11, wherein the pharmaceutically active compound is a corticoid, an antimycotic, salicylic acid, an alpha- or betahydroxy acid, and/or linolenic acid; wherein the vitamin is Vitamin E, or Vitamin K; and wherein the vitamin analog is Calcipotriol, or Tacalcitol.

13. The skin care formulation according to claim 1 for use in the prophylaxis and treatment of dry, sensitive skin or the therapy of eczematous skin and psoriatic skin.

14. A method of manufacturing a hypoallergenic and non-irritant skin care formulation comprising the steps of:

a) preparing an oil phase by melting:

1-8 wt % cetearyl octanoate, 1-5 wt % dicaprylyl ether, 6-20 wt % caprylic/capric triglyceride, 1-4 wt % polyglyceryl-3-diisostearate and 2-6 wt % polyglyceryl-2-dipolyhydroxystearate, b) preparing a water phase by heating purified water and dissolving therein 0.2-2 wt % magnesium sulfate, 0-2 wt % lactic acid and 0.5-7 wt % sodium lactate while stirring and adjusting the pH value of the resulting solution with lactic acid to about 4.4-4.8;

c) preparing a water-in-oil emulsion by transferring the melted oil phase from step (a) to the heated water phase of step (b) and, while stirring and homogenizing, cooling the emulsion down to room temperature while applying a vacuum of about −0.6 to −0.9 bar.

15. The method of claim 14, wherein step (a) and step (b) are performed at a temperature of about 75-85° C. and wherein step (c) comprises the steps of transferring the oil phase of step (a) into the water phase of step (b) while stirring at about 40 min-' at 75-85° C., cooling the emulsion down to about 58-62° C. while stirring and homogenizing at 3000 min 71, cooling the emulsion further down to about 38-42° C. while stirring and homogenizing at 4000 min-1, cooling the emulsion further down to about 23-27° C. while stirring, and discharging the emulsion into appropriate containers.

* * * * *

UNITED STATES PATENT AND TRADEMARK OFFICE

CERTIFICATE OF CORRECTION

PATENT NO. : 7,604,812 B2
APPLICATION NO. : 10/450666
DATED : October 20, 2009
INVENTOR(S) : Patrick Franke It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1442 days.

Signed and Sealed this

Fourteenth Day of December, 2010

David J. Kappos

*Director of the United States Patent and Trademark Office*